United States Patent
Sweeney

(10) Patent No.: US 7,634,307 B2
(45) Date of Patent: Dec. 15, 2009

(54) METHOD AND APPARATUS FOR TREATMENT OF DISCOGENIC PAIN

(75) Inventor: Patrick J. Sweeney, Flossmoor, IL (US)

(73) Assignee: Spinal Generations, LLC, Olympia Fields, IL (US)

( * ) Notice: Subject to any disclaimer, the term of this patent is extended or adjusted under 35 U.S.C. 154(b) by 51 days.

(21) Appl. No.: 11/393,054

(22) Filed: Mar. 30, 2006

(65) Prior Publication Data

US 2007/0238977 A1  Oct. 11, 2007

(51) Int. Cl.
*A61B 5/05* (2006.01)
*A61N 5/10* (2006.01)

(52) U.S. Cl. .................. 600/427; 600/411; 378/65

(58) Field of Classification Search .............. 600/427, 600/410
See application file for complete search history.

(56) References Cited

U.S. PATENT DOCUMENTS

| | | | |
|---|---|---|---|
| 4,624,846 A * | 11/1986 | Goldenberg | ............... 424/1.49 |
| 5,317,616 A | 5/1994 | Swerdloff et al. | |
| 5,427,097 A | 6/1995 | Depp | |
| 5,442,675 A | 8/1995 | Swerdloff et al. | |
| 5,548,627 A | 8/1996 | Swerdloff et al. | |
| 5,673,300 A | 9/1997 | Reckwerdt et al. | |
| 5,851,182 A * | 12/1998 | Sahadevan | .................. 600/407 |
| 6,032,066 A * | 2/2000 | Lu et al. | ...................... 600/407 |
| 6,366,802 B1 | 4/2002 | Haber et al. | |
| 6,560,311 B1 | 5/2003 | Shepard et al. | |
| 6,618,467 B1 | 9/2003 | Ruchala et al. | |
| 6,661,870 B2 | 12/2003 | Kapatoes et al. | |
| 6,778,850 B1 | 8/2004 | Adler et al. | |
| 7,150,710 B2 * | 12/2006 | Haber et al. | .................. 600/9 |
| 2002/0032378 A1 * | 3/2002 | Henderson et al. | .......... 600/427 |
| 2004/0006070 A1 * | 1/2004 | Hassenbusch et al. | ....... 514/220 |
| 2004/0127963 A1 | 7/2004 | Uchida et al. | |
| 2005/0197564 A1 * | 9/2005 | Dempsey | .................... 600/411 |

OTHER PUBLICATIONS

Andersson, Gunnar B.J. et al., "The Orthopaedic Forum: Intervertebral Disc Degeneration," *The Journal of Bone & Joint Surgery*, Apr. 2006, cover page and pp. 895-899, vol. 88-A, No. 4.
"Intervertebral Disc Degeneration, AAOS/NIH/ORS Workshop, Sep. 15-18, 2005," *The Journal of Bone & Joint Surgery*, vol. 88-A, Supplement 2, Apr. 2006, 119 pages.
Woeltjen et al., "The History, Current Treatment, and Future Outlook of Minimally Invasive Posterior Lumbar Disc Surgery," © 2005 UnderstandSurgery.com, 13 pages.
XKnife™ RT web page, Integra Radionics, 2 pages, printed from www.radionics.com on Jul. 10, 2006.
Radionics XKnife™ RT 3 brochure, 3 pages, printed from www.radionics.com on Jul. 10, 2006.

* cited by examiner

*Primary Examiner*—Eric F Winakur
*Assistant Examiner*—Michael T Rozanski
(74) *Attorney, Agent, or Firm*—Foley & Lardner LLP

(57) ABSTRACT

A method of treating discogenic back pain in a patient includes the steps of acquiring an image of at least a portion of the patient's spine, locating the spinal disc causing the back pain, and identifying a treatment volume encompassing at least a portion of the spinal disc. The method further includes prescribing a radiation dose to be delivered to the treatment volume, providing a radiation therapy machine, positioning the patient in the radiation therapy machine, programming the radiation therapy machine to deliver the radiation dose to the treatment volume, and delivering the radiation dose to the treatment volume.

9 Claims, 4 Drawing Sheets

METHOD AND APPARATUS FOR TREATMENT OF DISCOGENIC PAIN

FIELD OF THE INVENTION

The present invention relates to the use of radiation to treat back pain such as that caused by spinal disc disorders. In particular, the present invention relates to an apparatus for and method of treatment of discogenic pain using radiation.

BACKGROUND OF THE INVENTION

The spinal column is comprised of interlocking vertebrae separated by intervertebral discs. The spine provides load-bearing support for one-half of the body's mass and it protects the nerves of the spinal column. The intervertebral discs provide shock absorption and facilitate the bending of the spine.

The combination of the vertebrae and discs at each vertebral segment allows for motion of the spine, in particular, flexing, rotation, and extension. The motion and support functions of the spine, in combination with the many interlocking parts and nerves associated with the spinal column, can result in back pain due to various reasons.

Most back pain arises in the lumbar region of the back. Back pain may result from strain on the back due to overexertion or may be due to poor posture or an injury to the spine. Chronic back pain is often due to a disorder originating in or from an intervertebral disc (i.e. discogenic pain). Such conditions can include bulging, herniated, or ruptured discs. A bulging, herniated or ruptured disc can trigger a response from proximate nerves, causing the pain sensation. Even after a herniated disc heals, the anatomy of the disc may not return to normal and may continue to cause pain. Even in the case where a disc is not herniated, chronic pain may present itself as people age because the annulus fibrosus begins to decay and the resulting small tears in the wall are infiltrated by nerves and blood vessels, causing pressure and chronic pain.

Intervertebral discs have an outer annulus fibrosus that surrounds the inner nucleus pulposus. A bulging or herniated disc is a situation where the nucleus pulposus herniates outward through the annulus fibrosus. The annulus fibrosus contains nerves, and the nociceptors and mechanoreceptors associated with the nerves respond to the disc herniation by providing a pain sensation. The pain receptors are concentrated along the posterior wall of the disc and the pain may result from the disc herniation but may also result from internal disc disruption, possibly involving partial tears in the multi-layered annulus fibrosus. Pain may also result from a disc fragment that remains exterior to the annulus fibrosus after the herniated disc recedes.

There are several non-surgical approaches that may be used to treat back pain. These include heating the affected area, certain types of exercise, medication, and electrical nerve stimulation. However, non-surgical treatments are often ineffective in treating chronic back pain.

There are a number of minimally invasive surgical procedures that are used to treat back pain with varying degrees of success. Intradiscal electrothermal therapy (IDET), also called intradiscal electrothermal annuloplasty, involves the application of heat directly to the inside of the disc via a needle that is inserted into the disc and heated at the desired location. Radiofrequency annuloplasty is another surgical method in which radiofrequency thermal energy is delivered to the affected area of the disc via a needle. Laser discectomy involves using a laser to vaporize a portion of the nucleus pulposus to decrease pressure in the disc. Thermal discoplasty utilizes a needle to deliver heat to the nucleus pulposus to decrease the pressure in the disc.

Other conventional surgical approaches are less minimally invasive. These include discectomy, in which all or part of the disc is removed in an effort to reduce pressure on the affected nerves; disc replacement, in which the disc is replaced with an artificial disc; and spinal fusion, in which the affected disc is removed and the two adjoining vertebrae are fused together.

Certain of the conventional treatments are designed to ablate or remove disc material to reduce the pressure in the disc. These include the discectomy procedures, including laser discectomy and radiofrequency or thermal discoplasty, also referred to as disc nucleoplasty. Other techniques attempt to treat the disc directly using thermal or radiofrequency energy, such as the IDET and radiofrequency annuloplasty procedures. It is not known exactly why the procedures that attempt to directly treat the disc, such as IDET, work. It is theorized that the methods may aid in the repair of tears in the annulus fibrosus, but the procedures may also destroy nociceptors in the treated area, thus disrupting their ability to sense pressure and transmit pain.

Each of the conventional approaches for treating back pain has certain disadvantages. In particular, each of the surgical approaches, even those that are minimally invasive, require penetration of the skin with surgical instruments to approach the area to be treated, even where the primary surgical instrument is a catheter or needle. Further, there are risks associated with the conventional surgical approaches that are inherent in any operation on the spine. Further still, the cause of the back pain may be inoperable due to the anatomy of the spine. Finally, all of the present approaches to treatment of back pain exhibit varying degrees of success, especially where the precise reason why the selected treatment method accomplishes its goal is not exactly known. Presently, spinal fusion, the most invasive of the conventional surgical approaches, is the preferred approach when less invasive methods are not successful.

There is a need for a back pain treatment that addresses one or more of the disadvantages of conventional approaches. In particular, there is a need for a back pain treatment that is non-invasive, less expensive than conventional surgical treatments, and able to treat back pain that is otherwise inoperable.

It would be desirable to provide a system and/or method that satisfies one or more of the aforementioned needs or provides other advantageous features. Other features and advantages will be made apparent from the present specification. The teachings disclosed extend to those embodiments that fall within the scope of the claims, regardless of whether they accomplish one or more of the aforementioned needs.

SUMMARY OF THE INVENTION

The invention relates to a method of treating discogenic back pain in a patient. The method includes the steps of acquiring an image of at least a portion of the patient's spine, locating the spinal disc causing the back pain, and defining a treatment volume encompassing a portion of the spinal disc. The method further includes the steps of prescribing a radiation dose to be delivered to the treatment volume, providing a radiation therapy machine, and positioning the patient in the radiation therapy machine. Further still, the method includes the steps of programming the radiation therapy machine to deliver the radiation dose to the treatment volume and delivering the radiation dose to the treatment volume.

The invention further relates to a discogenic back pain treatment device having a patient support, a radiation source, and a radiation delivery mechanism coupled to the radiation source. The discogenic back pain treatment device further includes a treatment planning computer adapted to control the radiation delivery mechanism and programmed to deliver radiation from the radiation source to a treatment volume encompassing at least a portion of a spinal disc.

The invention further relates to a method for treating pain resulting from a herniated spinal disc using the discogenic back pain treatment device. The method includes the steps of contacting a medical clinic having a radiation therapy machine to schedule a visit, visiting the medical clinic, assuming a position on the patient support, and inactivating one or more nerves in a treatment volume encompassing at least a portion of the herniated disc by receiving radiation from the radiation source to the treatment volume.

The invention is capable of other embodiments and of being practiced or carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION OF THE PREFERRED EMBODIMENTS

Figure 1:
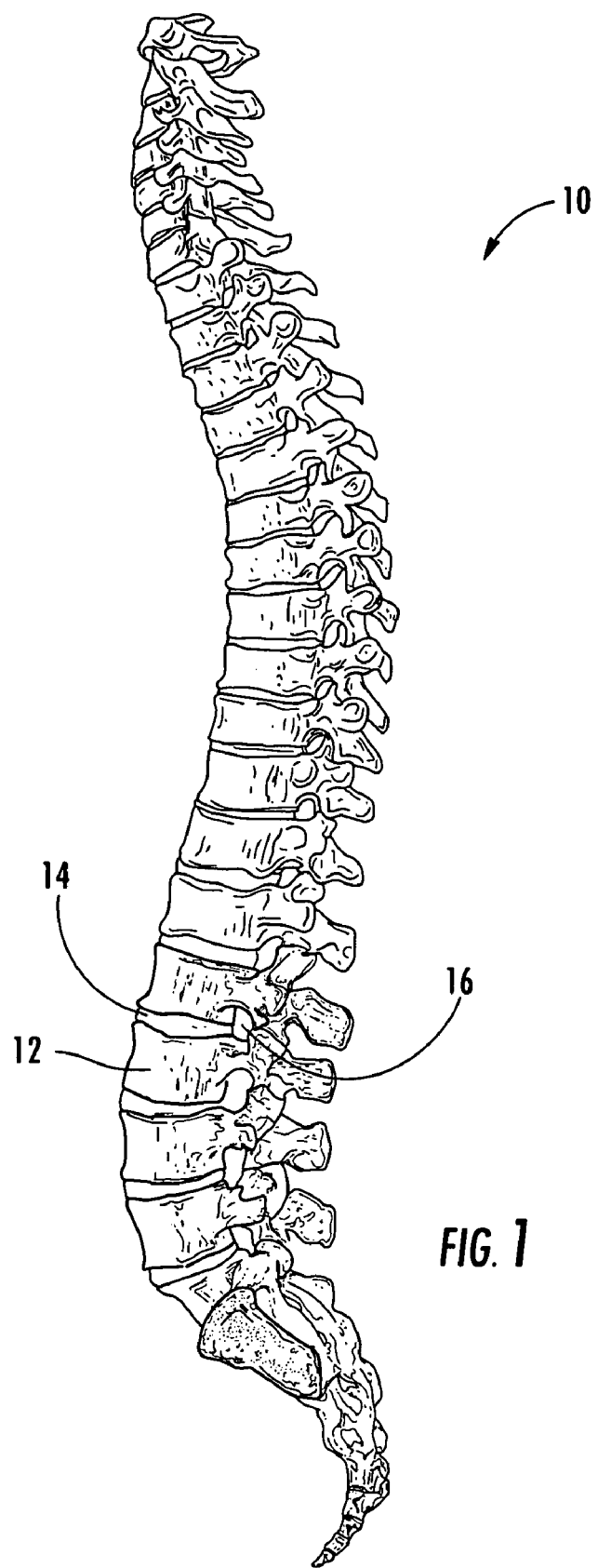
FIG. 1 is a side elevation view of a spine.

Referring to FIG. 1, the spine 10 includes vertebrae 12 separated by intervertebral discs 14. A vertebral canal 16 extends along successive vertebrae and houses the spinal cord (not shown).

Figure 2:
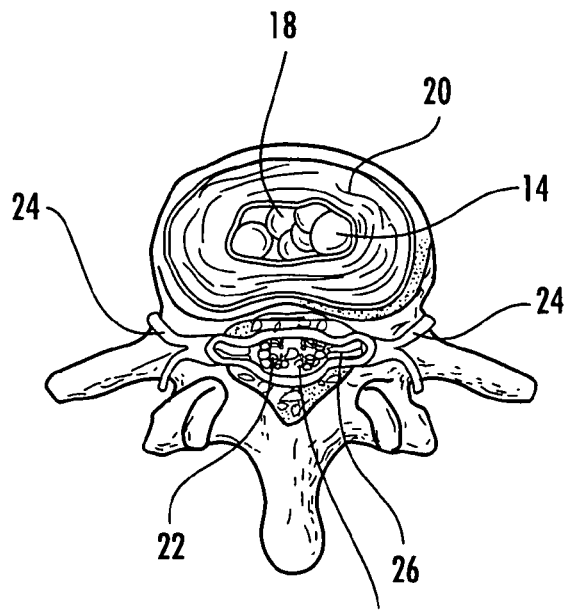
FIG. 2 is a sectional view of a portion of the lumbar portion of a spine including an intervertebral disc.
Figure 3:
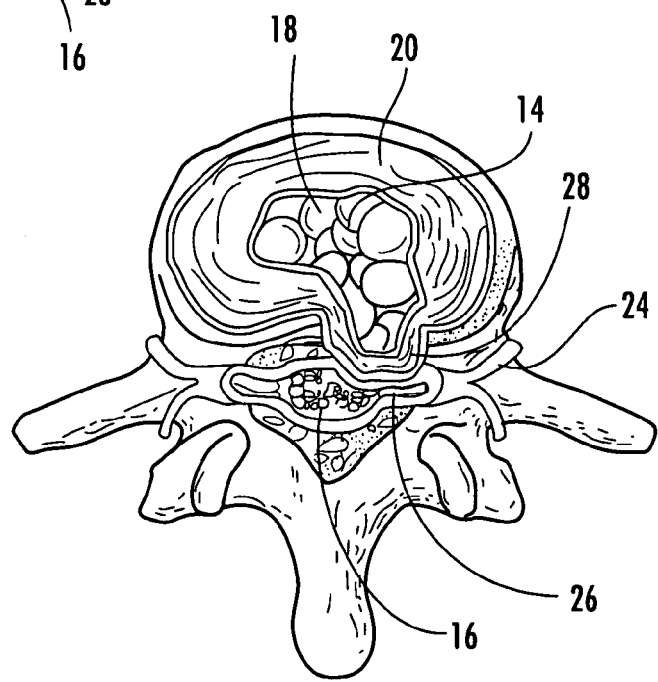
FIG. 3 is a sectional view of a portion of the lumbar portion of a spine including a partially herniated intervertebral disc.

Referring to FIG. 2, an intervertebral disc 14 includes an inner nucleus pulposus 18 and an outer annulus fibrosus 20. The annulus fibrosus 20 is made up of a number of bands that are arranged in a series of concentric layers to retain the nucleus pulposus 18 and aid in resisting other forces placed on the spine 10. In the lumbar portion of the spine 10, the cauda equina 22 runs through the vertebral canal 16. Spinal nerves 24 extend outwardly from the cauda equina 22, with nerve roots 26 proximate the cauda equina 22. While a lumbar vertebra and associated disc are shown in FIGS. 2-4, the invention is equally applicable to other vertebrae and discs in the spine.

The outer portion of the annulus fibrosus 20 is innervated by the sinuvertebral nerve (not shown). The sinuvertebral nerve also innervates other structures in the epidural space. As discussed above, the nociceptors in the annulus fibrosus 20 transmit pain due to herniation of the intervertebral disc 14 or other discogenic causes. For example, as shown in FIG. 3, the nucleus pulposus 18 may bulge outward, possibly due to degradation in the fibers making up the concentric rings of the annulus fibrosus 20. The bulging disc 14 may apply pressure on nerves proximate the bulge 28. Such pressure may result in radiating pain down a patient's leg. The entry into the vertebral canal 16 of the intervertebral disc 14 material may also cause toxic damage to the nerves in the area, resulting in pain.

Figure 4:
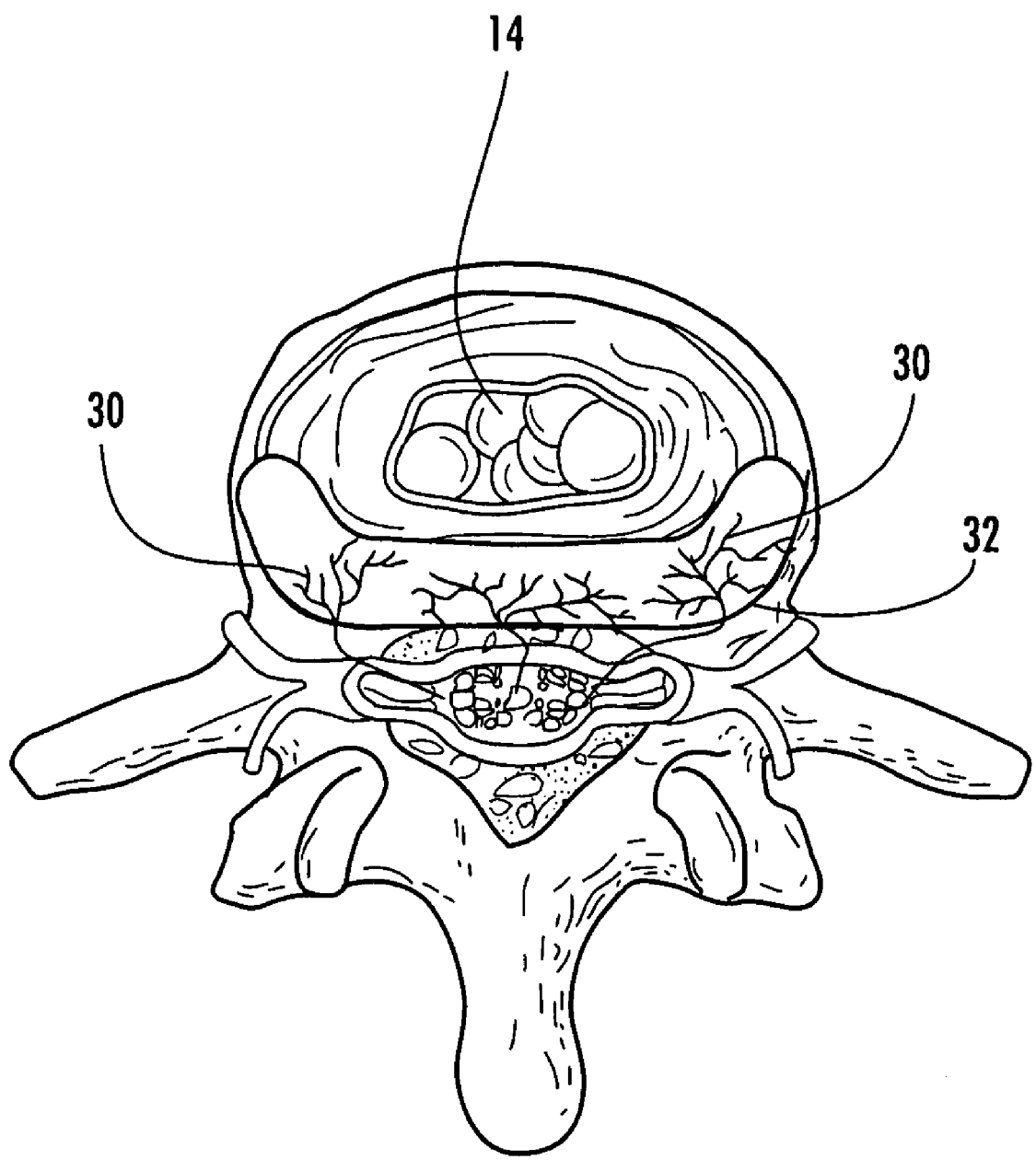
FIG. 4 is a sectional view of a portion of the lumbar portion of a spine including an intervertebral disc.

Referring to FIG. 4, the nociceptors 30 populating the outer portion of the annulus fibrosus 20 may transmit impulses resulting in the sensation of pain. Such nociceptors 30 are typically concentrated along the posterior wall of the disc 14. A treatment volume 32 may be identified that contains a number of the nociceptors 30 causing the pain sensation. Depopulation of the nociceptors 30 in the treatment volume 32 may result in a decrease or cessation of the pain originating from the treatment volume 32. It is theorized that certain conventional minimally invasive procedures, such as IDET, result in the thermocoagulation of nociceptors within the walls of the intervertebral disc being treated and therefore result in the reduction of pain. The treatment volume 32 may also include a portion of the intervertebral disc where blood vessels have invaded, such as the area of a tear in the annular wall of the disc. Such invading vasculature can cause back pain.

Figure 5:
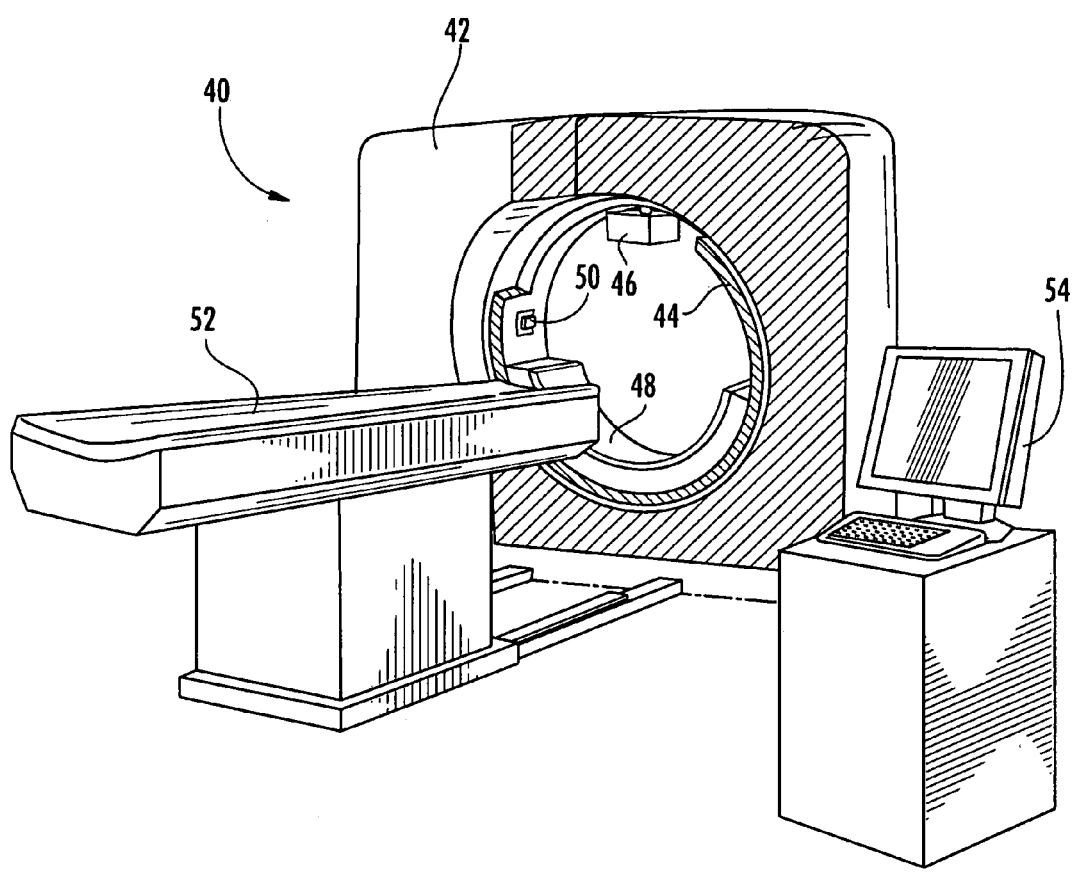
FIG. 5 is a schematic perspective view of a radiation therapy machine with a cut-away portion showing the gantry.

Referring to FIGS. 4 and 5, according to an exemplary embodiment of the invention, a radiation therapy machine 40 is used to deliver radiation to the treatment volume 32 in order to treat unremitting back pain. The radiation is intended to depopulate or inactivate the nerves providing the pain sensation, eliminate invading vasculature, and/or shrink disc material to reduce pressure in the area. In a preferred embodiment, the radiation therapy machine 40 is designed to utilize conformal radiotherapy to deliver the radiation to the treatment volume 32. Due to the sensitive structures proximate the treatment volume 32, in particular the spinal cord and cauda equina, ideally a form of image guided radiation therapy is utilized. One such image guided radiation therapy machine is the TomoTherapy HI-ART® system available from TomoTherapy Incorporated of Middleton, Wis.

In an exemplary embodiment, where an image-guided radiation therapy approach is utilized, the radiation therapy machine 40 has a rotating gantry 44 within a housing 42. An x-ray source 46 and corresponding detector 48 used for acquiring data to construct CT images of the patient are mounted on the gantry 44 along with a radiation delivery mechanism 50 used to deliver the desired dose to the treatment volume 32. The radiation delivery mechanism 50 is a rotating radiation output port on the gantry 44 in the embodiment of FIG. 5. A radiation source, e.g. linear accelerator or Cobalt-60 source, generates the radiation that is delivered via the radiation delivery mechanism 50. A patient support, shown as table 52, is configured to support the patient (not shown) within the rotating gantry 44 and to slide the patient through the open center portion of the gantry 44 in order to acquire a spiral CT scan of the patient simultaneously with the delivery of radiation in a helical fashion to the desired treatment volume 32. A computer workstation 54 may be utilized to control the radiation therapy machine 40 as well as to display the acquired images.

Other types of radiation therapy or radiosurgery equipment may also be utilized to deliver a prescribed radiation dose to the treatment volume 32. Examples of such devices include linear accelerators and x-ray machines. One machine using a linear accelerator that may be useful in a preferred embodiment is a CYBERKNIFE® stereotactic radiosurgery system that utilizes a radiation delivery mechanism in the form of a robotic arm to deliver a radiation beam from many different angles to the target area. The CYBERKNIFE® stereotactic radiosurgery system is available from Accuray Incorporated of Sunnyvale, Calif.

In order to determine whether the radiation therapy machine 40 may be utilized to treat lower back pain, the cause of the pain must first be diagnosed. Various methods for performing such a diagnosis are known, and include discography, which involves the injection of a radio-opaque dye into the spinal disc, followed by an x-ray image to determine whether the disc at issue is herniated or degraded in some way. A computed tomography (CT) or magnetic resonance imaging (MRI) scan may also be used to reconstruct a three-dimensional image of the area thought to be causing the pain to identify the condition causing the pain. Other types of imaging procedures, such as PET or SPECT, may also be utilized to identify the intervertebral disc causing the pain.

Referring again to FIG. 4, once the disc causing the pain has been identified along with the reason for the pain, the treatment volume 32 may be defined. In an exemplary embodiment, the treatment volume 32 is a three-dimensional region encompassing the posterior side of the annulus fibrosus 20 containing the offending nociceptors and/or the inflamed area causing the pain.

Once the treatment volume 32 has been defined, the physician treating the patient may prescribe a radiation therapy plan. In an exemplary embodiment, the radiation therapy plan or "treatment plan" involves delivering a specified radiation dose to the treatment volume, ideally using a stereotactic approach in order to spare issues outside of the treatment volume 32 to the extent possible. The radiation may be delivered to the treatment volume 32 in a single treatment or may be fractionated to deliver a portion of the prescribed dose over the course of several treatments. In an alternative embodiment, a fluid such as a dye may be injected into the disc space to concentrate the effect of the radiation delivered to the treatment volume.

In an exemplary embodiment, the workstation 54 is a treatment planning computer that is loaded with treatment planning software that may be used to calculate a suitable method for delivering the prescribed radiation dose to the treatment volume 32. In a preferred embodiment, the radiation is delivered from multiple positions relative to the treatment volume 32 such that the radiation beams travel through different tissues en route to the treatment volume 32. Ideally, the primary routes to the treatment volume should include certain "treatment portals" that do not include sensitive structures and therefore can accept a larger radiation dose. In this fashion, the radiation therapy machine 40 is programmed to properly deliver the radiation dose to the treatment volume 32. Definition of the treatment volume 32 and creation of the treatment plan may include an assessment of sensitive regions (e.g. radiosensitive tissues) proximate to the desired treatment volume and according modifications to the treatment volume 32 and/or treatment plan to ensure a lower radiation dose to sensitive areas.

Once the treatment volume 32 has been defined, and the treatment plan created, the patient may be positioned on the table 52 for delivery of radiation to the treatment volume 32. Prior to delivery of the radiation, the location of the patient may be identified utilizing the on-board CT scanner or other type of imaging device on a similar machine. Verification of the position of the patient is especially important due to the proximity of sensitive structures in the spine. Once the patient's position has been verified, the radiation therapy machine 40 may be used to deliver the prescribed radiation dose to the treatment volume 32.

The utilization of radiation to treat discogenic pain requires the programming of treatment planning software used to control the radiation therapy machine 40 in order to deliver radiation to the treatment volume 32. While radiation therapy is presently used to treat tumors found in the spine, such tumors are not typically found in the intervertebral discs. In one embodiment of the invention, similar doses and radiation energies are used to treat discogenic pain as are presently used in cancer treatments, but the radiation dose necessary to depopulate and/or inactivate the offending nociceptors 30 and/or eliminate invading vasculature may differ from the radiation dose necessary to kill tumor cells. Therefore, a lower radiation dose may be used to treat discogenic pain as compared to the total overall doses used to treat tumors. Fractionation may also be utilized in radiation treatment of discogenic pain.

Utilization of radiation therapy machine 40 to treat discogenic pain is non-invasive and may use currently available radiation therapy equipment with modifications in accordance with the invention described herein. In an exemplary embodiment, the radiation therapy machine 40 is owned by a medical clinic, such as a clinic specializing in the treatment of back pain. A patient may contact the clinic to set up an appointment to visit the clinic for diagnosis and/or treatment of the back pain, perhaps in response to advertisements or information provided by the clinic or other organization (e.g. advertisements in magazines, in newspapers, on billboards, or via television, radio, or the internet). Multiple treatment visits will be necessary in the case of a fractionated treatment plan.

Because conformal radiotherapy using machines such as the TomoTherapy HI-ART® or Accuray CYBERKNIFE® systems identified above delivers a radiation dose to a defined three-dimensional volume within the body while sparing proximate tissues to the extent possible, it may be possible to treat discogenic symptoms using radiation therapy where conventional surgical methods are unavailable. Further still, utilization of radiation therapy does not have the inherent risks associated with conventional spine surgery options, such as the spinal fusion surgical procedures that are currently utilized to treat chronic lower back pain.

While the detailed drawings and specific examples given herein describe various exemplary embodiments, they serve the purpose of illustration only. It is to be understood that the invention is not limited in its application to the details of construction and the arrangements of components set forth in the preceding description or illustrated in the drawings. For example the methods may be performed in a variety of sequences of steps. Furthermore, other substitutions, modifications, changes, and omissions may be made in the design, operating conditions, and arrangements of the exemplary embodiments without departing from the scope of the invention as expressed in the appended claims.

What is claimed is:

1. A method of treating discogenic back pain in a patient, comprising:
   acquiring an image of at least a portion of the patient's spine;
   locating the spinal disc causing the back pain;
   defining a treatment volume encompassing at least a portion of one or more nerves transmitting impulses that result in the sensation of the back pain caused by the spinal disc;
   prescribing a radiation dose to be delivered to the treatment volume;
   providing a radiation therapy machine;
   positioning the patient in the radiation therapy machine;
   configuring the radiation therapy machine to deliver the radiation dose to the treatment volume; and
   delivering the radiation dose to the portion of one or more nerves within the treatment volume.

2. The method of claim 1, wherein the image is acquired using at least one of a computed tomography scanner and an MRI system.

3. The method of claim 1, wherein the delivering the radiation dose step comprises delivering a portion of the radiation dose in each of multiple treatment sessions until the total radiation dose has been delivered.

4. The method of claim 1, wherein the radiation therapy machine uses a linear accelerator to produce radiation.

5. The method of claim 1, wherein the delivering the radiation dose step comprises delivering multiple beams of radiation to the treatment volume from different directions.

6. The method of claim 1, further comprising injecting a fluid into the treatment volume to concentrate the effect of the radiation.

7. The method of claim 1, further comprising:
identifying a radiosensitive area; and
configuring the radiation therapy machine to avoid the radiosensitive area when delivering the radiation dose.

8. The method of claim 7, wherein the radiosensitive area is avoided by delivering the radiation dose through one or more treatment portals extending through non-radiosensitive areas to reach the treatment volume.

9. The method of claim 1, wherein the radiation therapy machine utilizes x-rays or gamma rays to deliver the radiation dose to the treatment volume.

* * * * *